United States Patent [19]

Ogata et al.

[11] Patent Number: 4,820,831
[45] Date of Patent: Apr. 11, 1989

[54] PROCESS FOR PREPARING 4,4'-DIHYDROXYDIPHENYL SULFONE HAVING HIGH PURITY

[75] Inventors: Eiji Ogata; Koji Ono, both of Wakayama; Nobuyuki Nate, Kainan, all of Japan

[73] Assignee: Konishi Chemical Industry Co., Ltd., Wakayama, Japan

[21] Appl. No.: 10,095

[22] PCT Filed: Apr. 17, 1986

[86] PCT No.: PCT/JP86/00194
§ 371 Date: Dec. 12, 1986
§ 102(e) Date: Dec. 12, 1986

[87] PCT Pub. No.: WO86/06370
PCT Pub. Date: Nov. 6, 1986

[30] Foreign Application Priority Data

Apr. 19, 1985 [JP] Japan .................. 60-84875

[51] Int. Cl.⁴ .................................. C07C 147/10
[52] U.S. Cl. ....................................... 568/33
[58] Field of Search ............................ 568/33

[56] References Cited

U.S. PATENT DOCUMENTS 3,366,692 1/1968 Orem ..................... 568/33

FOREIGN PATENT DOCUMENTS 2030566 4/1980 United Kingdom .

OTHER PUBLICATIONS

Mitsubishi, Derwent Abstract of Japanese patent 50-116446, published Sep. 11, 1975.
Konishi, Derwent Abstract of Japanese patent 51-98239, published Aug. 39, 1976.
E. Ogata et al., Chemical Abstracts, vol. 85, No. 192367z (1976), Highly pure 4,4'-dihydroxydiphenyl sulfone.

Primary Examiner—Mary E. Ceperley
Attorney, Agent, or Firm—Armstrong, Nikaido, Marmelstein & Kubovcik

[57] ABSTRACT

The process of the present invention is a process for preparing 4,4'-dihydroxydiphenyl sulfone by subjecting phenol, and a sulfonating agent or phenolsulfonic acid to a dehydration reaction in the presence of a solvent, subsequently maintaining the reaction system at a temperature of between 100° to 200° C. and removing the solvent from the reaction system to cause the dehydration reaction to further proceed while allowing 4,4'-dihydroxydiphenyl sulfone to separate out and to subject dissolved 2,4'-dihydroxydiphenyl sulfone formed as a by-product to an isomerization reaction for converting the by-product to 4,4'-dihydroxydiphenyl sulfone, and eventually removing the solvent and the unreacted phenol from the system substantially entirely to complete the isomerization reaction, the process being characterized in that an aromatic sulfonic acid represented by the formula

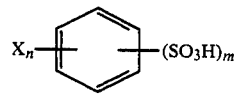

wherein X is a halogen atom, n is 0, 1 or 2, and m is 1 of 2 is caused to be present in the reaction system. 4,4'-Dihydroxydiphenyl sulfone can be produced by the process with a high purity and in a high yield.

6 Claims, No Drawings

PROCESS FOR PREPARING 4,4'-DIHYDROXYDIPHENYL SULFONE HAVING HIGH PURITY

TECHNICAL FIELD

The present invention relates to a process for preparing 4,4'-dihydroxydiphenyl sulfone having a high purity.

BACKGROUND ART 4,4'-Dihydroxydiphenyl sulfone is excellent in resistance to heat and oxidation, stability to light, etc. and is therefore an important chemical which is in increasing use in recent years as a substitute for bisphenol A in the field of plastics such as polyester resins, epoxy resins and polycarbonate resins. The 4,4'-dihydroxydiphenyl sulfone for such use must be at least 99% in purity.

The industrial processes heretofore known for producing 4,4'-dihydroxydiphenyl sulfone include one wherein phenol and sulfuric acid are subjected to a dehydration reaction. This process, however, gives a large amount of 2,4'-dihydroxydiphenyl sulfone as an isomer by-product along with 4,4'-dihydroxydiphenyl sulfone and involves difficulty in isolating 4,4'-dihydroxydiphenyl sulfone from the resulting isomer mixture, so that the products generally obtained invariably contain about 20 wt. % of the by-product. Accordingly, the 4,4'-dihydroxydiphenyl sulfone obtained by the process in no way fulfils the above requirement.

Various processes have therefore been proposed for preparing high-purity 4,4'-dihydroxydiphenyl sulfone. For example, Examined Japanese Patent Publications SHO 38-5274, SHO 43-24660, SHO 47-43936, etc. disclose processes wherein the 4,4'-dihydroxydiphenyl sulfone obtained by the above conventional process and containing a large amount of the isomer is recrystallized with a solvent. Any of these processes nevertheless relates to the separation and purification of the product resulting from the dehydration of phenol and sulfuric acid, accordingly inevitably permits the dehydration to produce about 20% of the isomer, consequently gives the desired 4,4'-dihydroxydiphenyl sulfone in a reduced yield and requires an additional purification procedure and further cumbersome treatment of the separated residue containing a large quantity of 2,4'-dihydroxydiphenyl sulfone.

DISCLOSURE OF THE INVENTION

Carrying out extensive research to overcome the foregoing drawbacks, we conceived of obaining 4,4'-dihydroxydiphenyl sulfone with a high purity in a high yield by improving the dehydration reaction itself between phenol and sulfuric acid and conducted a large number of experiments based on this concept. Consequently, we found it possible to prepare high-purity 4,4'-dihydroxydiphenyl sulfone in a high yield by a single process, by reacting phenol with sulfuric acid in the presence of a solvent for dehydration while almost completely isomerizing the resulting by-product 2,4'-dihydroxydiphenyl sulfone to 4,4'-dihdroxydiphenyl sulfone (see Examined Japanese Patent Publication SHO 55-8972 and corresponding U.S. Pat. No. 4,162,270). However, our subsequent research revealed that the dry solid product 4,4'-dihydroxydiphenyl sulfone obtained by this process, although almost free from the by-product 2,4'-dihydroxydiphenyl sulfone, contained as an impurity about 5 wt. % of trihydroxytriphenyl disulfone (hereinafter referred to as the "tri-compound"), i.e. the reaction product of phenolsulfonic acid and 4,4'-dihydroxydiphenyl sulfone or 2,4'-dihydroxydiphenyl sulfone, resulting from the dehydration reaction between phenol and sulfuric acid, that the tri-compound was difficult to separate from 4,4'-dihydroxydiphenyl sulfone and that the separation of the tri-compound from 4,4'-dihydroxydiphenyl sulfone relatively lowered the yield of 4,4'-dihydroxydiphenyl sulfone.

In view of the situation, we have made improvements in the above process and consequently found that the below-specified aromatic sulfonic acid, if present in the reaction system of phenol and sulfuric acid, makes it possible to almost completely isomerize the 2,4'-dihydroxydiphenyl sulfone resulting from the reaction to 4,4'-dihydroxydiphenyl sulfone and is also effective in greatly inhibiting formation of the tri-compound and in causing the dehydration reaction to proceed nearly 100%, consequently giving 4,4'-dihydroxydiphenyl sulfone with a high purity and in a high yield. Thus, the present invention has been accomplished.

An object of the present invention is to provide a process for preparing 4,4'-dihydroxydiphenyl sulfone which has a high purity and which is reduced in the contents of 2,4'-dihydroxydiphenyl sulfone and in the tri-compound.

Another object of the present invention is to provide a process for preparing 4,4'-dihydroxydiphenyl sulfone in a high yield.

Other features of the invention will become apparent from the following description.

The present invention provides a process for preparing high-purity 4,4'-dihydroxydiphenyl sulfone by subjecting phenol, and a sulfonating agent or phenolsulfonic acid to a dehydration reaction in the presence of a solvent, subsequently maintaining the reaction system at a temperature of between 100° to 200° C. and removing the solvent from the reaction system to cause the dehydration reaction to further proceed while allowing 4,4'-dihydroxydiphenyl sulfone to separate out and to subject dissolved 2,4'-dihydroxydiphenyl sulfone formed as a by-product to an isomerization reaction for converting the by-product to 4,4'-dihydroxydiphenyl sulfone, and eventually removing the solvent and the unreacted phenol from the system substantially entirely to complete the isomerization reaction, the process being characterized in that an aromatic sulfonic acid represented by the formula

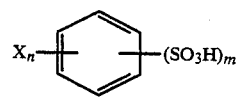 (1)

wherein X is a halogen atom, n is 0, 1 or 2, and m is 1 or 2 is caused to be present in the reaction system.

According to the present invention, phenol and a sulfonating agent or phenolsulfonic acid are subjected to a dehydration reaction and an isomerization reaction in the presence of a solvent. The invention is characterized in that the aromatic sulfonic acid is caused to be present in the reaction system. The aromatic sulfonic acid may be added to the system when the dehydration reaction is to be effected or when the isomerization reaction is to be conducted.

The aromatic sulfonic acid of the formula (1) to be used in the invention can be any of a wide variety of those already known insofar as the acid does not participate in the reaction between phenol and the sulfonating agent or the like and is stable in the reaction system. Examples of such aromatic sulfonic acids are benzenesulfonic acid, chlorobenzene-4-sulfonic acid, chlorobenzene-2-sulfonic acid, bromobenzene-4-sulfonic acid, bromobenzene-2-sulfonic acid, fluorobenzene-4-sulfonic acid, fluorobenzene-2-sulfonic acid, benzene-1,3-disulfonic acid, chlorobenzene-2,4-disulfonic acid, bromobenzene-2,4-disulfonic acid, fluorobenzene-2,4-disulfonic acid, 1,2-dichlorobenzene-4-sulfonic acid, 1,4-dichlorobenzene-2-sulfonic acid, 1,2-dibromobenzene-4-sulfonic acid, 1,4-dibromobenzene-2-sulfonic acid, etc. Especially suitable among these are benzenesulfonic acid, chlorobenzene-4-sulfonic acid, benzene-1,3-disulfonic acid, chlorobenzene-2,4-disulfonic acid, bromobenzene-4-sulfonic acid and fluorobenzene-4-sulfonic acid. According to the present invention, these aromatic sulfonic acids may be used singly, or at least two of them may be used in admixture. The aromatic sulfonic acid may be used in a catalytic amount. The amount of the acid is not limited specifically but can be suitably determined from a wide range. The amount is usually at least about 0.1 mole %, preferably about 0.5 to about 10 mole %, more preferably about 1 to about 5 mole %, based on one mole of the sulfonating agent or phenolsulfonic acid. Although no objection occurs in the reaction with use of an increased amount of the aromatic sulfonic acid, it is economically desirable to use up to about 10 mole % of the acid. While useful aromatic acids can be those commercially available, such an acid may be purified before practicing the process of the invention from a reaction mixture obtained from benzene or a benzene halide, and sulfuric acid, fuming sulfuric acid or like sulfonating agent. Alternatively, the reaction mixture is usable as it is. In the latter case, the unreacted sulfonating agent in the reaction mixture is usable as it is as the sulfonating agent for preparing the dihydroxydiphenyl sulfone. The aromatic sulfonic acid achieves the contemplated effect of the invention if used in a small amount, can therefore be discarded after the reaction almost without entailing any economical problem but is reusable after the separation of the desired product when required.

The sulfonating agent to be used in the present invention can be any of those heretofore known, such as concentrated sulfuric acid, sulfuric anhydride, fuming sulfuric acid, chlorosulfonic acid, etc. Among these, concentrated sulfuric acid is especially desirable.

The dehydration reaction of the present invention can be conducted easily by the conventional method while subjecting the resulting water and a solvent to azeotropic distillation usually at 120° to 220° C., preferably about 140° to 180° C., and removing the water and refluxing the solvent. The solvent to be used for the reaction is one which is inert under the reaction conditions and boils at a suitable pressure and in which 4,4'-dihydroxydiphenyl sulfone is less soluble than 2,4'-dihydroxydiphenyl sulfone, preferably with a great solubility difference between the sulfones. Further for industrial operation, it is advantageous that the solvent be distillable at a suitable rate. Examples of typical solvents fulfilling these requirements are chlorobenzene, dichlorobenzene, trichlorobenzene, chlorotoluene, diethylbenzene, decalin, tetralin, tetrachloroethane, n-octane, n-decane, etc. Among these, chlorobenzene and chlorotoluene are especially desirable. These solvents are used singly, or at least two of them are used in admixture. The amount of the solvent to be used is not limited specifically provided that the dehydration reaction and isomerization reaction of the invention can be conducted. It is used in an amount conventionally used, for example, usually in about 0.1 to about 5 times, preferably about 0.2 to about 2 times, the amount by weight of phenol.

The ratio of phenol to the sulfonating agent or phenolsulfonic acid to be used in the process of the invention is not limited specifically but can be determined suitably from a wide range. Usually, it is suitable to use the former at least in a stoichiometric ratio to the latter. For example, when the sulfonating agent is used, usually at least about 2 moles, preferably about 2 to about 3 moles, of phenol is used per mole of the sulfonating agent. Further when phenolsulfonic acid is used, usually at least about 1 mole, preferably about 1 to about 2 moles, of phenol is used per mole of the acid.

When the dehydration reaction is conducted under the foregoing conditions, 4,4'-dihydroxydiphenyl sulfone and an isomer thereof, i.e. 2,4'-dihydroxydiphenyl sulfone, are produced, with isomerization equilibrium established between the two. In a state in which 4,4'- and 2,4'-dihydroxydiphenyl sulfones are completely dissolved at a reaction temperature of around 180° C., 4,4'-dihydroxydiphenyl sulfone and 2,4'-dihydroxydiphenyl sulfone are formed in the ratio of 76:24 at which isomerization equilibrium is reached.

In a desired stage of the dehydration reaction and thereafter, the temperature of the reaction system is maintained at about 100° to about 200° C., preferably 120° to 170° C., and the solvent is removed from the reaction system to gradually decrease the amount of the solvent present in the system. Eventually, the solvent and the unreacted phenol are removed from the reaction system substantially completely. As the amount of solvent decreases in this step, 4,4'-dihydroxydiphenyl sulfone dissolving in the solvent in the isomerization equilibrium ratio separates out as isolated from the solution system, whereby the ratio between 4,4'-dihydroxydiphenyl sulfone and 2,4'-dihydroxydiphenyl sulfone dissolving in the solvent is changed to a value different from the point of equilibrium. In this state, the isomerization of the 2,4'-isomer to 4,4'-dihydroxydiphenyl sulfone is promoted until isomerization equilibrium is reached. Thus, with a decrease in the quantity of solvent, pure 4,4'-dihydroxydiphenyl sulfone alone repeatedly separates out while the 4,4'-dihydroxydiphenyl sulfone and 2,4'-dihydroxydiphenyl sulfone dissolving in the solvent are maintained in isomerization equilibrium, consequently decreasing the 2,4'-isomer content of the entire reaction system. In this way, the isomerization reaction proceeds as the amount of solvent decreases. Although the amount of the by-product, i.e. the tri-compound, increases in this step in the absence of catalyst (the aromatic sulfonic acid), we have found that the increase can be inhibited greatly by the presence of the catalyst. Moreover, the catalyst acts effectively in the above step for a further progress of the dehydration reaction, permitting the reaction to proceed almost completely when the step is completed. When the solvent is finally removed from the reaction system substantially entirely, the contents of the impurity compounds, i.e. 2,4'-dihydroxydiphenyl sulfone and the tri-compound, can be reduced to about 2%. In the absence of the catalyst, on the other hand, the contents of 2,4'-dihydroxydiphenyl sulfone and the tri-compound are about 7%. Although the timing of the isomerization reaction procedure is not limited specifically, it is desirable to start the reaction in the final stage of the dehydration reaction.

The isomerization reaction temperature of the foregoing step, if below 100° C., results in exceedingly retarded isomerization which is undesirable. At such a reaction temperature, 4,4'-dihydroxydiphenyl sulfone will separate out with the removal of the solvent, but little or no isomerization occurs, nor does the dehydration reaction proceed. If the reaction temperature exceeds 200° C., the 4,4'-dihyroxydiphenyl sulfone once separating out dissolves to convert to 2,4'-dihydroxydiphenyl sulfone, hence undesirable. The reaction temperature is easily adjustable by suitably controlling the internal pressure of the system according to the heating temperature, etc. Preferably, the solvent is removed from the reaction gradually. More specifically, it is desirable to remove the solvent over a period of about 3 to about 8 hours. If the solvent is removed too rapidly, 2,4'-dihydroxydiphenyl sulfone also separates out along with 4,4'-dihydroxydiphenyl sulfone, making it difficult for the isomerization reaction to proceed.

The above procedure is executed until the solvent and the unreacted phenol are removed from the reaction system substantially entirely. As the solvent is removed during the procedure, 4,4'-dihydroxydiphenyl sulfone separates out, and the isomerization reaction proceeds at the same time to convert 2,4'-dihydroxydiphenyl sulfone to 4,4'-dihydroxydiphenyl sulfone. The isomerization reaction is completed when the solvent is completely removed from the system. If the reaction is terminated with some of the solvent remaining in the system, unreacted 2,4'-dihydroxydiphenyl sulfone remains undesirably.

The dry solid product obtained on completion of the reaction is treated by a usual method. For example, the product is dissolved in an aqueous alkali solution, and the solution is treated with active carbon and then neutralized, whereby 4,4'-dihydroxydiphenyl sulfone can be obtained with a purity of about 99%.

With the process of the present invention, the aromatic sulfonic acid is present in the system for the dehydration reaction of phenol with a sulfonating agent or phenolsulfonic acid. The presence of the acid promotes the dehydration reaction, consequently entailing the advantages of a greatly shortened reaction time and favorable progress of the reaction even at a relatively low temperature. Further according to the process of the present invention, the presence of the aromatic sulfonic acid in the reaction system makes it possible for the subsequent isomerization reaction to almost completely isomerize a by-product of the dehydration reaction, i.e. 2,4'-dihydroxydiphenyl sulfone, to 4,4'-dihydroxydiphenyl sulfone, with the formation of the tri-compound greatly inhibited. As a result, the desired 4,4'-dihydroxydiphenyl sulfone can be produced with a high purity and in a high yield. Furthermore, the aromatic sulfonic acid, when made present in the isomerization reaction system, promotes the isomerization reaction, thereby resulting in advantages such as a great reduction in the reaction time and favorable progress of the reaction even at a relatively low temperature.

EXAMPLES

The present invention will become more apparent from the following examples and comparative examples.

EXAMPLE 1

To a mixture of 216 g (2.30 moles) of phenol, 100 g (1.00 mole) of 98% sulfuric acid and 57 g of chlorobenzene was added 11.9 g (5 mole % based on the sulfuric acid used) of benzene-1,3-disulfonic acid, and the mixture was heated with stirring. At about 135° C., the reaction mixture boiled, azeotropically giving a fraction of chlorobenzene and the resulting water. The fraction was subjected to condensation and thereby separated into two phases. The organic phase was returned to the reactor continuously. Four hours after the start of distillation, i.e. when the internal temperature of the reactor reached 158° C. with the amount of the aqueous phase increasing to 37 ml, the reaction mixture was found to contain 4,4'-dihydroxydiphenyl sulfone, 2,4'-dihydroxydiphenyl sulfone and the tri-compound in the ratio of 86.2:13.4:0.4.

Over a period of 5 hours following this stage, the reaction mixture was distilled to dryness to recover the resulting water, unreacted phenol and chlorobenzene while maintaining the reaction temperature at 135° to 140° C. and adjusting the pressure reduction. When analyzed by liquid chromatography, the dry product was found to contain 4,4'-dihydroxydiphenyl sulfone, 2,4'-dihydroxydiphenyl sulfone and the tri-compound in the ratio of 98.1:1.6:0.3. The yield of the 4,4'-dihydroxydiphenyl sulfone was 96.6% based on the sulfuric acid.

COMPARATIVE EXAMPLE 1

The same procedure as in Example 1 was repeated with the exception of not using any benzene-1,3-disulfonic acid. When the internal temperature reached 158° C. with the amount of the aqueous phase increasing to 37 ml 8 hours after the start of distillation, the reaction mixture was found to contain 4,4'-dihydroxydiphenyl sulfone, 2,4'-dihydroxydiphenyl sulfone and the tri-compound in the ratio of 81.0:18.4:0.6.

In the same manner as in Example 1, the reaction mixture was then distilled to dryness. When analyzed by liquid chromatography, the dry product was found to contain 4,4'-dihydroxydiphenyl sulfone, 2,4'-dihydroxydiphenyl sulfone and the tri-compound in the ratio of 88.3:8.6:3.1. The yield of the 4,4'-dihydroxydiphenyl sulfone was 80.4% based on the sulfuric acid.

COMPARATIVE EXAMPLE 2

The same procedure as in Example 1 was repeated with the exception of not using any benzene-1,3-disulfonic acid. When the internal temperature reached 158° C. with the amount of the aqueous phase increasing to 37 ml 8 hours after the start of distillation, the reaction mixture was found to contain 4,4'-dihydroxydiphenyl sulfone, 2,4'-dihydroxydiphenyl sulfone and the tri-compound in the ratio of 81.0:18.4:0.6.

Subsequently, the reaction mixture was distilled to dryness in the same manner as in Example 1 except that the reaction temperature was maintained at 160° to 165° C. When analyzed by liquid chromatography, the dry product was found to contain 4,4'-dihydroxydiphenyl sulfone, 2,4'-dihydroxydiphenyl sulfone and the tri-compound in the ratio of 92.7:2.1:5.2. The yield of the 4,4'-dihydroxydiphenyl sulfone was 84.8% based on the sulfuric acid.

EXAMPLE 2

A mixture of 216 g (2.30 moles) of phenol, 100 g (1.00 mole) of 98% sulfuric acid and 57 g of chlorobenzene was heated with stirring. At about 135° C., the reaction mixture boiled, azeotropically giving a fraction of chlorobenzene and the resulting water. The fraction was subjected to condensation and thereby separated into two phases. The organic phase was returned to the reactor continuously. When the internal temperature of the reactor reached 159° C. with the amount of the aqueous phase increasing to 37 ml 8 hours after the start of distillation, the reaction mixture was found to contain 4,4'-dihydroxydiphenyl sulfone, 2,4'-dihydroxydiphenyl sulfone and the tri-compound in the ratio of 81.0:18.4:0.6.

In this stage, the reaction temperature was lowered to 140° C., and 9.6 g (5 mole % based on the sulfuric acid used) of chlorobenzene-4-sulfonic acid was added to the mixture. The reaction mixture was then distilled to dryness over a period of 5 hours to recover the resulting water, unreacted phenol and chlorobenzene while maintaining the reaction temperature at 135° to 140° C. and adjusting the pressure reduction. When analyzed by liquid chromatography, the dry product was found to contain 4,4'-dihydroxydiphenyl sulfone, 2,4'-dihydroxydiphenyl suflone and the tri-compound in the ratio of 97.0:2.2:0.8. The yield of the 4,4'-dihydroxydiphenyl sulfone was 94.1% based on the sulfuric acid.

EXAMPLE 3

To a mixture of 230 g of phenol, 100 g of 98% sulfuric acid and 60 g of chlorobenzene was added benzenesulfonic acid in an amount of 5 mole % based on the sulfuric acid used, and the mixture was heated with stirring. The reaction mixture was thereafter treated in the same manner as in Example 1 to obtain a dry product. When analyzed by liquid chromatography, the product was found to contain 4,4'-dihydroxydiphenyl sulfone, 2,4'-dihydroxydiphenyl sulfone and the tri-compound in the ratio of 97.2:2.0:0.8. The yield of the 4,4'-dihydroxydiphenyl sulfone was 94.1% based on the sulfuric acid.

EXAMPLE 4

To a mixture of 207 g of phenol, 100 g of 98% sulfuric acid and 50 g of chlorobenzene was added chlorobenzene-4-sulfonic acid in an amount of 5 mole % based on the sulfuric acid used, and the mixture was heated with stirring. The reaction mixture was thereafter treated in the same manner as in Example 1 to obtain a dry product. When analyzed by liquid chromatography, the product was found to contain 4,4'-dihydroxydiphenyl sulfone, 2,4'-dihydroxydiphenyl sulfone and the tri-compound in the ratio of 97.9:1.7:0.4. The yield of the 4,4'-dihydroxydiphenyl sulfone was 95.7% based on the sulfuric acid.

A result comparable to the above was achieved when 1,2-dichlorobenzene-4-sulfonic acid was used in place of chlorobenzene-4-sulfonic acid.

EXAMPLE 5

To a mixture of 122 g of phenol, 174 g of phenolsulfonic acid and 56 g of o-chlorotoluene was added chlorobenzene-2,4-disulfonic acid in an amount of 2.5 mole % based on the sulfuric acid used, and the mixture was heated with stirring. The reaction mixture was thereafter treated in the same manner as in Example 1 to obtain a dry product. When analyzed by liquid chromatography, the product was found to contain 4,4'-dihydroxydiphenyl sulfone, 2,4'-dihydroxydiphenyl sulfone and the tri-compound in the ratio of 97.1:2.2:0.7. The yield of the 4,4'-dihydroxydiphenyl sulfone was 94.7% based on the phenolsulfonic acid.

We claim:

1. In a process for preparing 4,'-dihydroxydiphenyl sulfone by condensation of phenolsulfonic acid and phenol, wherein the condensation is effected by heating in an inert, non-aqueous solvent while removing the water of dehydration by azeotropic distillation, followed by heating at a temperature between 100° and 200° C. for a period of at least three hours while slowly removing solvent by distillation, to isomerize 2,4'-dihydroxydiphenyl sulfone to 4,4'-dihydroxydiphenyl sulfone, the improvement comprising adding an aromatic sulfonic acid represented by the formula:

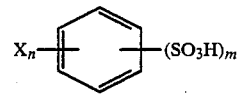

wherein X is a halogen atom, n is 0, 1 or 2, and m is 1 or 2, in an isomerization catalyst amount.

2. The process according to claim 1, wherein the aromatic sulfonic acid is added after azeotropic distillation has been completed.

3. The process according to claim 1, wherein said phenol sulfonic acid is produced in situ by reacting phenol and a sulfonating agent.

4. A process as defined in claim 1 wherein the aromatic sulfonic acid is at least one acid selected from the group consisting of benzenesulfonic acid, chlorobenzene-4-sulfonic acid, chlorobenzene-2-sulfonic acid, bromobenzene-4-sulfonic acid, bromobenzene-2-sulfonic acid, fluorobenzene-4-sulfonic acid, fluorobenzene-2-sulfonic acid, benzene-1,3-disulfonic acid, chlorobenzene-2,4-disulfonic acid, bromobenzene-2,4-disulfonic acid, fluorobenzene-2,4-disulfonic acid, 1,2-dichlorobenzene-4-sulfonic acid, 1,4-dichlorobenzene-2-sulfonic acid, 1,2-dibromobenzene-4-sulfonic acid and 1,4-dibromobenzene-2-sulfonic acid.

5. A process as defined in claim 1 wherein the aromatic sulfonic acid is present in the reaction system in the ratio of about 0.5 to about 10 mole % per mole of the sulfonating agent or phenolsulfonic acid.

6. A process as defined in claim 4 wherein the aromatic sulfonic acid is present in the reaction system in the ratio of about 0.5 to about 10 mole per mole of the sulfonating agent or phenolsulfonic acid.

* * * * *